US009161709B2

(12) United States Patent
Kawchuk

(10) Patent No.: US 9,161,709 B2
(45) Date of Patent: Oct. 20, 2015

(54) BIOLOGICAL SKELETAL SYSTEM MONITORING

(76) Inventor: Greg Kawchuk, Edmonton (CA)

( * ) Notice: Subject to any disclaimer, the term of this patent is extended or adjusted under 35 U.S.C. 154(b) by 829 days.

(21) Appl. No.: 12/994,112

(22) PCT Filed: May 22, 2009

(86) PCT No.: PCT/CA2009/000669
§ 371 (c)(1),
(2), (4) Date: Dec. 21, 2010

(87) PCT Pub. No.: WO2009/140756
PCT Pub. Date: Nov. 26, 2009

(65) Prior Publication Data
US 2011/0172566 A1 Jul. 14, 2011

Related U.S. Application Data

(60) Provisional application No. 61/055,748, filed on May 23, 2008.

(51) Int. Cl.
*A61B 5/11* (2006.01)
*A61B 5/00* (2006.01)
*A61B 8/08* (2006.01)

(52) U.S. Cl.
CPC ............ *A61B 5/1116* (2013.01); *A61B 5/0051* (2013.01); *A61B 5/4504* (2013.01); *A61B 5/4561* (2013.01); *A61B 5/4566* (2013.01); *A61B 5/6823* (2013.01); *A61B 5/6878* (2013.01); *A61B 8/08* (2013.01); *A61B 2562/043* (2013.01)

(58) Field of Classification Search
CPC .. A61B 5/4566; A61B 5/1104; A61B 5/1116; A61B 5/4561

USPC ................................... 600/552, 587, 594, 553
See application file for complete search history.

(56) References Cited

U.S. PATENT DOCUMENTS 4,489,729 A * 12/1984 Sorenson et al. ............. 600/447
4,762,134 A * 8/1988 Gala ............................. 600/594
5,626,615 A 5/1997 Keller
(Continued)

FOREIGN PATENT DOCUMENTS

JP   D2-S49-11484   10/1974
JP   S49-111484    10/1974
(Continued)

OTHER PUBLICATIONS

Colloca, Christopher J., et al. "Spinal manipulation force and duration affect vertebral movement and neuromuscular resopnses." 2006. Clinical Biomechanics. vol. 21. pp. 254-262.*
(Continued)

*Primary Examiner* — Max Hindenburg
(74) *Attorney, Agent, or Firm* — Frank J. Dykas; Dykas Law Offices, PLLC

(57) ABSTRACT

A method of monitoring target tissue of a biological skeletal system. The method comprises applying a mechanical excitation to a portion of the biological skeletal system to generate a mechanical wave that passes through the target tissue, the target tissue modulating the mechanical wave to produce a response of the target tissue to the mechanical wave, measuring the response; and determining structural or functional status of the target tissue from the response. A system for applying the method is also provided.

26 Claims, 12 Drawing Sheets

(56) References Cited

U.S. PATENT DOCUMENTS

| | | | |
|---|---|---|---|
| 5,653,733 A | 8/1997 | Keller | |
| 5,656,017 A | 8/1997 | Keller | |
| 5,897,510 A * | 4/1999 | Keller et al. | 600/594 |
| 5,921,929 A | 7/1999 | Goll | |
| 2002/0103432 A1 * | 8/2002 | Kawchuk | 600/437 |
| 2005/0119568 A1 | 6/2005 | Salcudean et al. | |

FOREIGN PATENT DOCUMENTS

| | | |
|---|---|---|
| JP | D3-S53-148189 | 12/1978 |
| JP | S53-148189 | 12/1978 |
| JP | D4-H09-238938 | 9/1997 |
| JP | H09-238938 | 9/1997 |

OTHER PUBLICATIONS

Keller, Tony S. et al. "Neuromechanical characterization of in vivo lumbar spinal manipulation. Part 1. Vertebral Motion." 2003. Journal of Manipulaive and Physiological Therapeutics. pp. 567-578.*

International Search Report for PCT/CA2009/000669, dated Aug. 27, 2009.

International Preliminary Report on Patentability for PCT/CA2009/000669, dated Nov. 23, 2010.

Japanese office action and translation of Japanese application corresponding to this pending application.

Supplementary European Search Report for 09749360.5—1506/2280647 PCT/CA2009000669 Dated Aug. 13, 2013.

* cited by examiner

| Set Number | Structural State | Damage location | Damage Magnitude | Number of collected trials | | | Number of training trials (mixed intensities) | Number of testing trials and trial numbers | Diagnostic expected to be |
|---|---|---|---|---|---|---|---|---|---|
| | | | | Intensity #1 | Intensity #2 | Intensity #3 | | | |
| 1 | HS1 | | | 10 | 10 | 10 | 24 | 6 (1-6) | 1 |
| 2 | DS1 | DL1 | DE1 | 5 | 5 | 5 | 12 | 3 (7-9) | 2 |
| 3 | HS2 | | | 10 | 10 | 10 | 24 | 6 (10-15) | 1 |
| 4 | DS2 | DL2 | DE1 | 5 | 5 | 5 | 12 | 3 (16-18) | 3 |
| 5 | HS3 | | | 10 | 10 | 10 | 24 | 6 (19-24) | 1 |
| 6 | DS3 | DL3 | DE1 | 5 | 5 | 5 | 12 | 3 (25-27) | 4 |
| 7 | HS4 | | | 10 | 10 | 10 | 24 | 6 (28-33) | 1 |
| 8 | DS4 | DL4 | DE1 | 5 | 5 | 5 | 12 | 3 (34-36) | 5 |
| 9 | HS5 | | | 10 | 10 | 10 | 24 | 6 (37-42) | 1 |
| 10 | DS5 | DL1 and DL3 | DE1 | 5 | 5 | 5 | 12 | 3 (43-45) | 2,4 |
| 11 | HS6 | | | 10 | 10 | 10 | 24 | 6 (46-51) | 1 |
| 12 | DS6 | DL2 and DL4 | DE1 | 5 | 5 | 5 | 12 | 3 (52-54) | 3,5 |
| 13 | HS7 | | | 10 | 10 | 10 | 24 | 6 (55-60) | 1 |
| 14 | DS7 | DL1 and DL4 | DE1 | 5 | 5 | 5 | 12 | 3 (61-63) | 2,5 |
| 15 | HS8 | | | 10 | 10 | 10 | 24 | 6 (64-69) | 1 |
| 16 | DS8 | DL1 | DE31 | 5 | 5 | 5 | 12 | 3 (70-72) | 2,6 |
| 17 | DS9 | DL1 | DE32 | 5 | 5 | 5 | 12 | 3 (73-75) | 2,7 |
| 18 | DS10 | DL1 | DE33 | 5 | 5 | 5 | 12 | 3 (76-78) | 2,8 |
| 19 | DS11 | DL4 | DE31 | 5 | 5 | 5 | 12 | 3 (79-81) | 5,6 |
| 20 | DS12 | DL4 | DE32 | 5 | 5 | 5 | 12 | 3 (82-84) | 5,7 |
| 21 | DS13 | DL4 | DE33 | 5 | 5 | 5 | 12 | 3 (85-87) | 5,8 |
| 22 | DS14 | DL3 | DE31 | 5 | 5 | 5 | 12 | 3 (88-90) | 4,6 |
| 23 | DS15 | DL3 | DE32 | 5 | 5 | 5 | 12 | 3 (91-93) | 4,7 |
| 24 | DS16 | DL3 | DE33 | 5 | 5 | 5 | 12 | 3 (94-96) | 4,8 |
| 25 | DS17 | DL2 | DE31 | 5 | 5 | 5 | 12 | 3 (97-99) | 3,6 |
| 26 | DS18 | DL2 | DE32 | 5 | 5 | 5 | 12 | 3 (100-102) | 3,7 |
| 27 | DS19 | DL2 | DE33 | 5 | 5 | 5 | 12 | 3 (103-105) | 3,8 |
| | | | | | | TOTAL TRIALS | 420 | 105 | |

FIG. 5

|  | Known condition → | Single FRF Trial | | Trials used to test network | | Structural States | |
|---|---|---|---|---|---|---|---|
| Neural network diagnosis ↓ | | + | − | + | − | + | − |
| Health State (HS) | + | 0 | 7 | x6 0 | x6 42 | x8 0 | x8 336 |
|  | − | 0 | 1 | x6 0 | x6 6 | x8 0 | x8 48 |
| Reversible Single Damage State (DS) | + | 1 | 0 | x3 3 | x3 0 | x4 12 | x4 0 |
|  | − | 7 | 0 | x3 21 | x3 0 | x4 84 | x4 0 |
| Reversible Dual Damage State (DS) | + | 2 | 0 | x3 6 | x3 0 | x3 18 | x3 0 |
|  | − | 6 | 0 | x3 18 | x3 0 | x3 54 | x3 0 |
| Irreversible Damage State (DS) | + | 2 | 0 | x3 6 | x3 0 | x12 72 | x12 0 |
|  | − | 6 | 0 | x3 18 | x3 0 | x12 216 | x12 0 |

|  | TOTAL | |
|---|---|---|
|  | + | − |
| + | 102 | 335 |
| − | 354 | 48 |
|  | 840 | |

FIG. 6

| Known condition → | | All Axes | | X Axis | | Y axis | | Z Axis | |
|---|---|---|---|---|---|---|---|---|---|
| Neural network diagnosis ↓ | | DS | HS | DS | HS | DS | HS | DS | HS |
| | | + - | + - | + - | + - | + - | + - | + - | + - |
| Pig 1 | DS + | 102/102 0/336 | | 101/102 0/336 | | 102/102 0/336 | | 102/102 0/336 | |
| | HS - | 0/354 48/48 | | 1/354 48/48 | | 0/354 48/48 | | 0/354 48/48 | |
| Pig 2 | DS + | 101/102 0/336 | | 102/102 0/336 | | 102/102 1/336 | | 101/102 0/336 | |
| | HS - | 1/354 48/48 | | 0/354 47/48 | | 0/354 47/48 | | 1/354 48/48 | |
| Pig 3 | DS + | 101/102 0/336 | | 102/102 0/336 | | 98/102 0/336 | | 101/102 0/336 | |
| | HS - | 0/354 48/48 | | 1/354 48/48 | | 0/354 48/48 | | 1/354 48/48 | |
| Pig 4 | DS + | 98/102 0/336 | | 98/102 0/336 | | 98/102 0/336 | | 100/102 0/336 | |
| | HS - | 2/354 48/48 | | 2/354 48/48 | | 2/354 48/48 | | 4/354 48/48 | |
| Pig 5 | DS + | 101/102 0/336 | | 102/102 0/336 | | 100/102 0/336 | | 99/102 0/336 | |
| | HS - | 0/354 48/48 | | 0/354 48/48 | | 0/354 48/48 | | 2/354 48/48 | |
| Pig 6 | DS + | 102/102 0/336 | | 103/102 0/336 | | 100/102 0/336 | | 102/102 1/336 | |
| | HS - | 0/354 48/48 | | 0/354 48/48 | | 1/354 48/48 | | 0/354 48/48 | |
| All Pigs | DS Misassignments | 7 0 | | 6 0 | | 12 1 | | 7 1 | |
| | HS Misassignments | 3 0 | | 4 1 | | 3 1 | | 8 0 | |
| | Total # errors | 10/5040 | | 11/5040 | | 17/5040 | | 16/5040 | |

FIG. 8

|  | All Axes | | X Axis | | Y axis | | Z Axis | |
|---|---|---|---|---|---|---|---|---|
|  | Sensitivity | Specificity | Sensitivity | Specificity | Sensitivity | Specificity | Sensitivity | Specificity |
| Pig 1 | 1.000 | 1.000 | 0.997 | 1.000 | 1.000 | 1.000 | 1.000 | 1.000 |
| Pig 2 | 0.997 | 1.000 | 1.000 | 1.000 | 1.000 | 0.997 | 0.997 | 1.000 |
| Pig 3 | 1.000 | 1.000 | 0.997 | 1.000 | 1.000 | 1.000 | 0.997 | 1.000 |
| Pig 4 | 0.994 | 1.000 | 0.994 | 1.000 | 0.994 | 1.000 | 0.989 | 1.000 |
| Pig 5 | 1.000 | 1.000 | 1.000 | 1.000 | 1.000 | 1.000 | 0.994 | 1.000 |
| Pig 6 | 1.000 | 1.000 | 1.000 | 1.000 | 0.997 | 1.000 | 1.000 | 0.997 |

FIG. 9

BIOLOGICAL SKELETAL SYSTEM MONITORING

CLAIM TO PRIORITY

This application claims the benefit of U.S. Provisional Application No. 61/055,748, filed May 23, 2008, and to PCT application number PCT/CA2009/000669, filed May 22, 2009, which claims priority to U.S. Provisional Application No. 61/055,748, filed May 23, 2008, the disclosures of which are incorporated by reference.

FIELD

Diagnostic medical systems

BACKGROUND

Many people suffer from back pain. It is often difficult to diagnose the cause of the back pain. In attempting to diagnose the cause of back pain, imaging devices such as ultrasound or x-ray machines can be used to obtain a picture of the structure of a patient's spine. However, the static view of the spine's structure may not be sufficient to evaluate the structural integrity or the functional capacity of the spine. The non-static alternative to evaluating the spine is to use a single point probe which applies a force (i.e. excitation) at a single point location and measures the response at that same location. This method is often inadequate to identify structural and functional defects that may relate to a subject's discomfort.

Although a relation between spinal structure and function is assumed, we have yet to understand how and when structural alterations occur and why these alterations may or may not lead to pathology and morbidity. One explanation for this deficiency of knowledge is a general inability to evaluate spinal structure. While many techniques are available to view spinal anatomy, they may not be sufficient to evaluate structural integrity or functional capacity. Specifically, various imaging techniques may lack the ability or resolution to visualize the structural change of importance. Even if structural alterations are visualized, their presence may not influence structural integrity or performance. Therefore, with few tools available to evaluate spinal structure, understanding its significance to spinal dysfunction, injury and pathology is considerably difficult as is finding a meaningful solution to the significant costs and morbidity associated with these conditions.

SUMMARY

There is provided a method of monitoring target tissue of a biological skeletal system, particularly a vertebral column. The method in one embodiment comprises applying a mechanical excitation to a portion of the biological skeletal system to generate a mechanical wave that passes through the target tissue, the target tissue modulating the mechanical wave to produce a response of the target tissue to the mechanical wave, measuring the response; and determining structural or functional status of the target tissue from the response.

There is also provided a system for monitoring the condition of target tissue of a biological skeletal system. The system in one embodiment comprises a mechanical signal generator for applying a mechanical excitation to a portion of the biological skeletal system to generate a mechanical wave that is capable of passing through the target tissue and being modulated by the target tissue to produce a response of the target tissue to the mechanical wave; one or more sensors adapted to be distributed at locations on the biological skeletal system for sensing the response; and a processing system connected to receive output of the one or more sensors and produce a representation of the response. The processing system may determine structural or functional status of the target tissue from the sensor output.

The response of the biological skeletal system may be measured using sensors at a plurality of locations on the biological skeletal system, for example distributed across the target tissue, such as a vertebral column, with the sensors sampled simultaneously.

These and other aspects of the device and method are set out in the claims, which are incorporated here by reference.

BRIEF DESCRIPTION OF THE DRAWINGS

Embodiments will now be described with reference to the figures, in which like reference characters denote like elements, by way of example, and in which:

FIG. 5 is a summary of exemplary structural states created in each test specimen. Structural states consist of a singular health state and damage states further characterized by damage location (L1-2 damage=DL1, L2-3 damage=DL2, L3-4 damage=DL3 and L4-5 damage=DL4) and damage magnitude (linked vertebrae=DE1, Scalpel stab=DE31, half disc transaction=DE32, full disc transaction=DE32). Also shown are the number of trials collected at each vibration intensity as well as the number of those trails used for training and testing the neural network. Finally, the expected diagnostic nodes assignments for each structural state are shown.

FIG. 6 is a potential number of diagnostic node assignments made by an exemplary neural network. In each case, the potential node assignments are grouped into four categories based on the known presence/absence of damage and the judgment of the neural network regarding the presence or absence of damage. The total number of potential assignments in these four categories are then given for a single trial, for the total number of trials used to test the neural network then the total number of trials based on all structural states. For the number of test trials used to train the neural network over all structural states, the neural network has the potential to make 840 judgments that can be broken down into true positives (102), true negatives (48), false positives (336) and false negatives (354).

FIG. 8 is an actual number of diagnostic node assignments made by the exemplary neural network expressed in terms of the total number of potential assignments (FIG. 6). DS=damage state and HS=health state. Results are reported for each animal tested and by the accelerometer axis under consideration. From these data, the total number of misassignments are reported using a denominator of the total number of potential assignments per animal (840) multiplied by 6 animals (5040);

FIG. 9 is the sensitivity and specificity of neural network diagnoses by animal and accelerometer axis.

DETAILED DESCRIPTION

Target tissue is the part of a biological skeleton system that a clinician or veterinarian wishes to study. The target tissue may be vertebra in a vertebral column. A mechanical excitation is applied by a mechanical excitation device such as a shaker to a portion of a biological skeletal system to generate a mechanical wave that passes through the target tissue. The mechanical wave is modulated by the target tissue to produce a response of the target tissue to the mechanical wave. Characteristics of the mechanical excitation may be measured at the application point, and at one or more sensors that measure the response of the biological skeletal system to the mechanical excitation. A processing system permits the determining of a property of the target tissue from the response.

The response, or output of the biological skeletal system, may be measured as soon as received which, due to propagation speeds of the signal, is a practically simultaneous output. In some embodiments, the mechanical excitation or signal input is a mechanical vibration which is applied to a single point on a vertebra of a patient's spine and the response is measured simultaneously at a number of different points on the patient's vertebra column. The method can be repeated for a range of different frequencies, such as, for example, frequencies in a range of 0 to 2000 Hz but may be higher. The excitation may be supplied in bursts, for example a burst of one second then a delay of one second before the next burst. Sensed responses resulting from the bursts may be averaged. The resulting data may be used to generate a frequency response function. The frequency response function can be used to diagnose changes and/or problems with the skeletal system.

Figure 1:
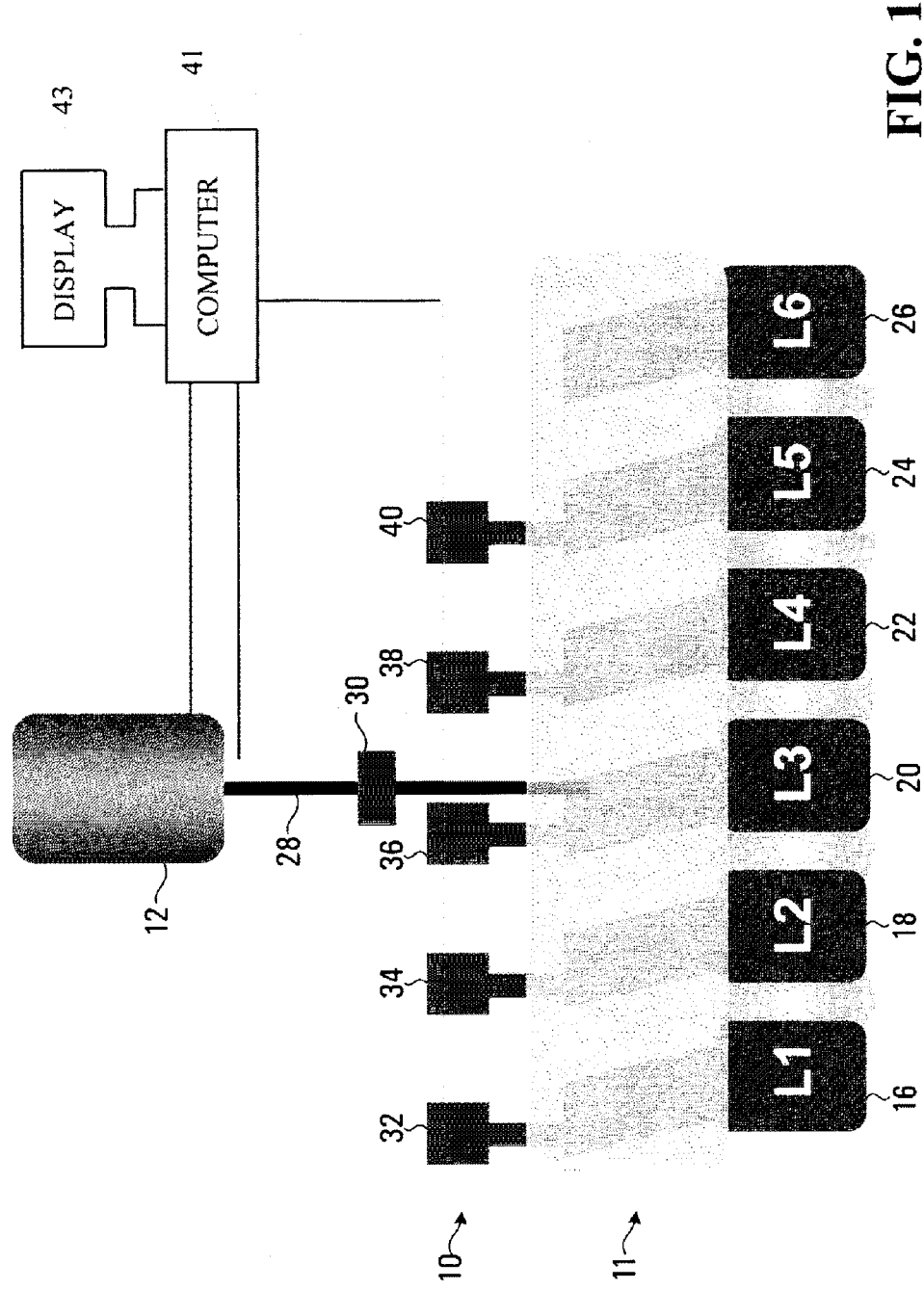
FIG. 1 is a schematic view of a system for monitoring the condition of target tissue of a biological skeletal system.

FIG. 1 provides a schematic view of a system 10 connected to a patient 11. The system 10 includes a mechanical signal generator 12. The signal generated by the signal generator 12 is a mechanical signal or excitation. In one embodiment, the signal generator 12 is an electro-mechanical shaker that is controlled by software to provide mechanical waves of a specific frequency range. These waves can be presented randomly over the frequency range or presented in increasing or decreasing order. The software can also control the displacement and/or loads created by the shaker. Other sources of excitation include piezo electric and hydraulic shakers, self-movement or surrounding environments. Any technology which provides an appropriate force and displacement may be used. The sensors may be accelerometers, laser vibrometers, displacement transducers, ultrasound detectors or other sensors suitable for detecting the response of a mechanical wave passing through a biological skeletal system and surrounding tissues.

The patient may be positioned in an upright weight bearing or other position of normal activity rather than reclined. This may have the advantage of providing measurements based on normal active, rather than static positioning.

The mechanical input need not be provided by a special purpose mechanical signal generator. Instead, the system may use a vibration source that exists in the subject's own environment. For example, the excitation could be provided by sitting in a car or running on a treadmill, in which case the car or treadmill coupled with the person's running motion is the mechanical signal generator. While these excitation sources may not provide a broad range of frequencies, such an excitation source can provide context specific information that would be valuable in diagnosing the environmental causes of, for example, a spinal problem.

In the embodiment of FIG. 1, the mechanical signal generator 12 is used to provide a controlled signal input. The signal generator 12 may be secured or anchored to a stationary/rigid object 42 such that the body of the shaker is for example suspended above the subject and does not move in response to its own vibration but rather only the output side of the generator 12 induces movement. This can provide a more controlled output from the generator 12. The generator 12 may be a single axis generator or a multi-axis signal generator. The generator may be singular or there may be multiple generators. It may be advantageous to have a shaker which generates vibrating at a broad range of frequencies, for example spanning at least 40 Hz.

As shown in FIG. 1, the signal generator 12 is connected to the patient 11 for applying a mechanical excitation to a portion of the biological skeletal system of the person to generate a mechanical wave that is capable of passing through the target tissue (here, a portion of the vertebral column). The patient 11 has a skin layer 14 and exemplary vertebrae 16, 18, 20, 22, 24 and 26 below the skin layer 14. As the mechanical wave passes through the target tissue, it is modulated by the target tissue and this modulation generates a response of the target tissue to the mechanical wave.

In the embodiment of FIG. 1, the signal generator 12 is connected directly to part of the skeletal system of the patient 11. In this embodiment, it is the vertebrae 20 of the patient 11. In the embodiment of FIG. 1, the connection is made by a rod 28. The rod 28, also known as a stinger, is a thin rod which is flexible about its longitudinal axis. The rod, for example, may be a metal rod or a plexiglass rod. In the embodiment of FIG. 1, the rod is screwed into the shaker or signal generator 12 at one end and clamped to a vertebrae 20 of the patient 11 at the other end. This may require an incision be cut through the skin layer 14 of the patient 11, or a needle may be inserted through the skin into the skeleton and a sensor attached to the needle. The embodiment of FIG. 1 could, for example, be used during surgery to analyze the results of a surgical treatment of the spine of the patient 11. The rod 28 could be connected at either or both ends or by other means such as clamping, clipping or simply abutting with applied pressure preload to keep it in place. A sensor or calibrated spring can be used in series with the stinget to measure or standardize the preload force. In other embodiments, the rod 28 may simply abut, be glued to, suction cupped to or otherwise attached to the skin layer 14 and not directly contact the vertebrae 20. Since the skin layer 14 over the vertebrae 16 to 26 is thin, the skin layer 14 does not completely mask the response and useful information may be obtained from the response detected through the skin layer 14. Other means of connecting the generator 12 to the patient 11 may also be used. For example, the generator 12 may be directly connected to the vertebrae 20 or another point of the skeletal system of the patient 11 such as the pelvis. It would be appreciated that vertebrae 20 of FIG. 1 is an exemplary input location and other input locations on the skeleton of the patient may be used.

In the embodiment of FIG. 1, a load cell 30 is mounted to the rod 28. The load cell 30 measures the signal which is actually delivered from the generator 12 to the patient 11. For example, the load cell 30 may measure amplitude, frequency and direction of the signal input to the patient by the generator 12. The load cell 30 further may be any means of quantifying the signal input. The load cell 30 measures the mechanical excitation applied to the portion of the biological excitation system to generate an input signal response. An accelerometer may be combined with the load cell 30 to take measurements from the same location that is being subject to mechanical excitation.

In the system 10, the output from the skeletal system as a result of the input signal is also measured. In the embodiment of FIG. 1, sensors or measurement devices 32, 34, 36, 38 and 40 are provided. The sensors 32-40 measure a response of the biological skeletal system to the mechanical excitation after the mechanical wave from the mechanical excitation has passed through at least a portion of the target tissue. The system 10 uses at least one measurement device at an output point which may be separate from the input point for the input signal. In the embodiment of FIG. 1, separate from the attachment for the rod 28, each of the measurement devices are connected to a different element of the skeletal system of the patient 11. In the embodiment of FIG. 1, each of the measurement devices 32, 34, 26, 38 and 40 are connected to one of the vertebrae 16, 18, 20, 22 and 24 of the patient 11 respectively. The measurement devices measure at least one parameter of a signal output at the point of connection to the patient 11 in response to the input signal from the generator 12. What is measured depends on the type of measurement device used. For example, the measurement devices 32, 34, 36, 38 and 40 may be accelerometers which measure the acceleration of their respective points in three axes. The devices may also measure in only one axis and may measure other parameters such as displacement and velocity. For example, an ultrasound machine can be used to measure displacement or velocity.

In the embodiment of FIG. 1, the measurement devices are screwed directly into the respective vertebrae. However, they may be clipped or attached to the vertebrae in any way or simply abut the vertebrae or the surface of the skin layer 14 over the vertebrae. Although five measurement devices are depicted in FIG. 1, it will be understood that a fewer number or more measurement devices may be used without deviating from the invention. The mechanical excitation device, outputs of the load cell 30 and the measurement devices 32, 34, 36, 38 and 40 may be connected to a processing device such as a computer 41 with display 43. Any conventional processing device may be used and the processing device may be made up of more than one module. The connections, represented by lines in the figures, between the devices are conventional communications cables. The sensors 32-40 may be arranged in parallel, each connected separately to the processing device 41 or serially, with each sensor passing along signals from sensors further from the processing device 41. The mechanical excitation device and sensors may be obtained from a suitable vendor along with required drivers and data collectors. The drivers and data collectors are not shown separately in the figures, but may be considered to be part of the sensors or the processing device.

Figure 1A:
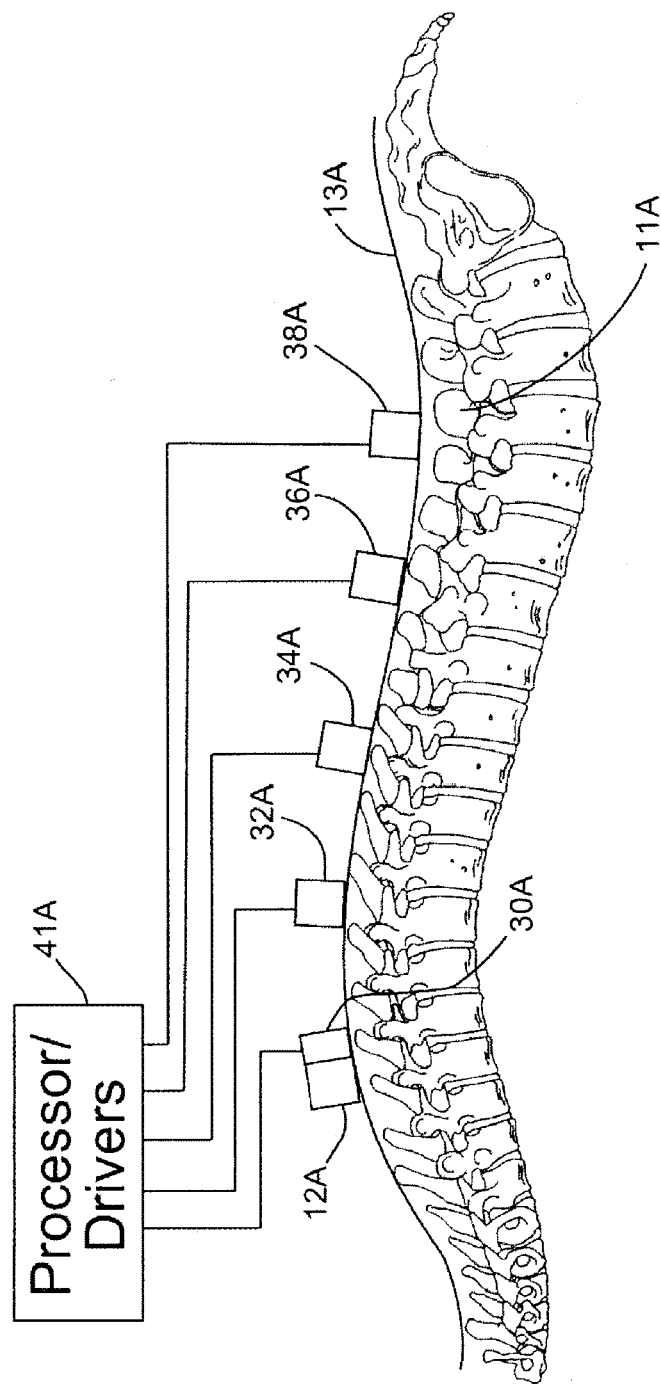
FIG. 1A shows a further embodiment of a system for monitoring the condition of target tissue of a biological skeletal system.

FIG. 1A shows a further embodiment of a skeleton monitoring system in which mechanical excitation from an excitation device 12A is applied through a skin layer 13A to a vertebral column 11A. The input response is sensed by sensor 30A, and sensors 32A-38A, which are secured to the skin layer 13A by various means such as straps or adhesive, directly or indirectly, such as through small disks or suction cups. In general, it is desirable to increase the surface area between the sensor and the subject when mounting sensors to the skin. Output of the sensors is delivered to processing device 41A. The embodiment of FIG. 1A works in the same manner as the embodiment of FIG. 1, except that the mechanical wave in the skeletal system 11A sensed through the skin suffers from frequency dependent attenuation as compared with a directly measured mechanical wave. It may be desirable to pre-load the mechanical excitation device to ensure that device does not break contact with the skin at any time during its stroke.

The processor 41 may be used to analyze the data output to develop a history of the response of the patient 11. The history can be used in various ways. A history can be taken for an individual and then stored and used to diagnose changes in that individual. Another option is to develop a history from a variety of different individuals and use that to diagnose problems in other individuals. The history can be developed by inputting signals at a range of frequencies and measuring the output at each frequency. Another option is to understand which parts of the resulting waveform correspond to problems in specific tissues then determine which tissues are involved in what manner to produce the patient's current waveform. The order of the frequencies can be randomized and may be repeated. The signal may be in one or several axes. By analyzing the response measured by the sensors, for example by comparing the response with a standard determined for example from a history of the response, the processing device 41 may determine a structural or functional status of the target tissue through which the mechanical wave from the mechanical excitation has passed. The structural or functional status may be an indication of a structural or functional defect, and may include the magnitude and location of the structural or functional defect. The processing device may use a neural network to determine characteristics of the target tissue from the response. The neural network is first trained by processing responses through the neural network that correlate to known characteristics of the skeletal system. By running a response from a target tissue through the trained neural network, the target tissue may be characterized. A simple characterization is to identify the target tissue as normal or not normal. The processing device 41 may also perform the analysis of the response by looking at statistical properties of the response, as for example from analysis of the power spectrum of a range of frequencies.

In one embodiment, the signal from the sensor 30 that characterizes the excitation (e.g. load cell) is used with each of the response sensor signals to compute a frequency response function (FRF) for each sensor signal. An analysis performed generates a frequency response function which may be plotted to develop a frequency response function for a range of different frequencies. Frequency response functions can also be used as the basis of other analysis techniques such as modal analysis.

Figure 2:
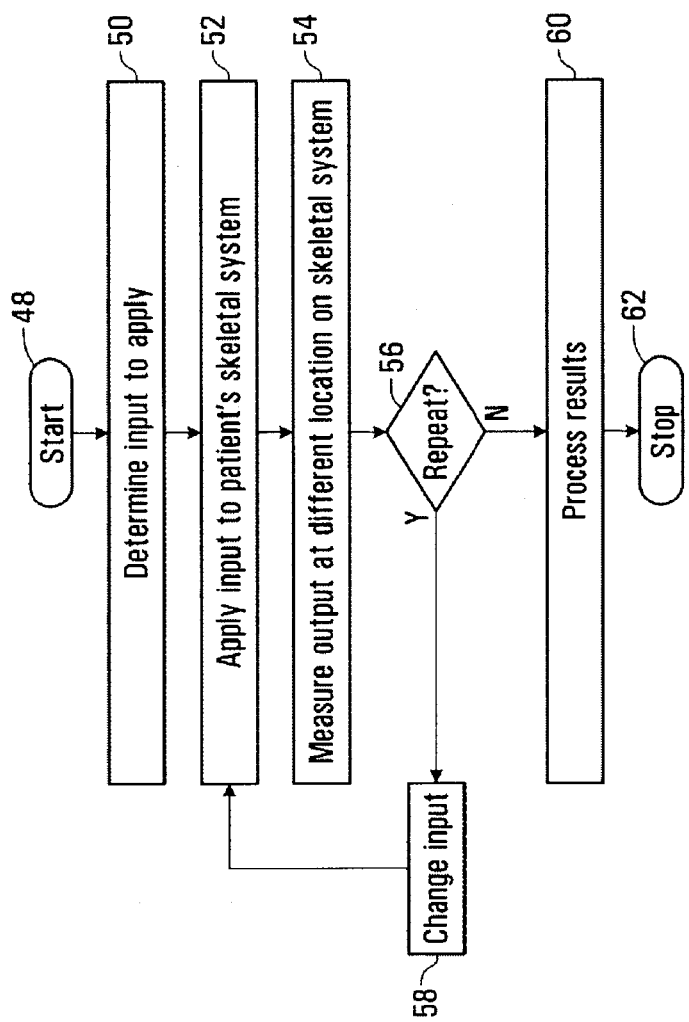
FIG. 2 is a flow diagram of a method for monitoring the condition of target tissue of a biological skeletal system.

FIG. 2 provides a flow chart of the operation of a system according to the invention beginning with the start 48. First, a signal input to the patient is determined at step 50. This may be, for example, be a mechanical vibration from a special purpose signal generator as discussed with respect to FIG. 1 or an environmental mechanical input which is measured. The input is then applied to a point on the skeletal system of the patient at step 52 as discussed in respect of FIG. 1. The duration may, for example, be approximately 10 seconds or less. For example, a vibratory input may be applied directly to one of the patient's vertebrae.

In the time domain transmissometry application, an output at least one other location on the patient's skeletal system is then measured at step 54. For example, the acceleration of several other vertebrae may be measured simultaneously in three axes in response to the input. Other options are discussed in the context of FIG. 1, including, for example, measuring displacement or velocity.

A decision is then made whether to repeat the measurement at step 56. The repetition at a variety of different frequencies, randomly applied, and possibly repeated, may be used. The frequency ranges may span at least 40 Hz. If there is a repeat then at step 58 the input may be changed so that a different frequency and possibly a different magnitude of the input is used. Alternatively, the same input may be repeated. The force applied may be up to 50 Newtons for example.

The steps 52, 54 and 58 can be repeated any number of times. For example, the force may be applied for 10 seconds and then repeated 10 times. The repeats may be put together into a testing session that consists of 1 continuous collection of data that lasts about 3 minutes.

The output data is then processed at step 60. It would be understood that the processing at step 60 can be conducted concurrently with the repeated step 58. The results can be processed to generate a frequency response function based on analysis of the input and the output signals. The frequency response function can then be used to chart the current condition of the skeletal system and changes in the skeletal system can then be determined by comparing a current frequency response function to historical data. Data for healthy and unhealthy skeletal systems may also be compared to diagnose problems with the unhealthy system. In particular, a number of healthy individuals and those with known problems may be measured to develop base lines against which others may be compared.

There is sufficient information in the frequency response function data to identify the structural status of the spine as well as injury locations, if data is collected from different locations, and magnitude.

In an embodiment of the system, a vibration is used as an input signal and a variety of different input frequencies are used. A single input may be provided and multiple outputs measured. An advantage of the system is that it can be non-invasive where the input signal and the output signal is provided by abutting the devices against the skeletal elements through the skin rather than cutting an incision through the skin. The input frequencies can be randomized when repeating the process to provide responses at a variety of different frequencies. Commercially available forced generators, measurement devices and load cells and connecting rods may be used.

Example 1

Figure 3:
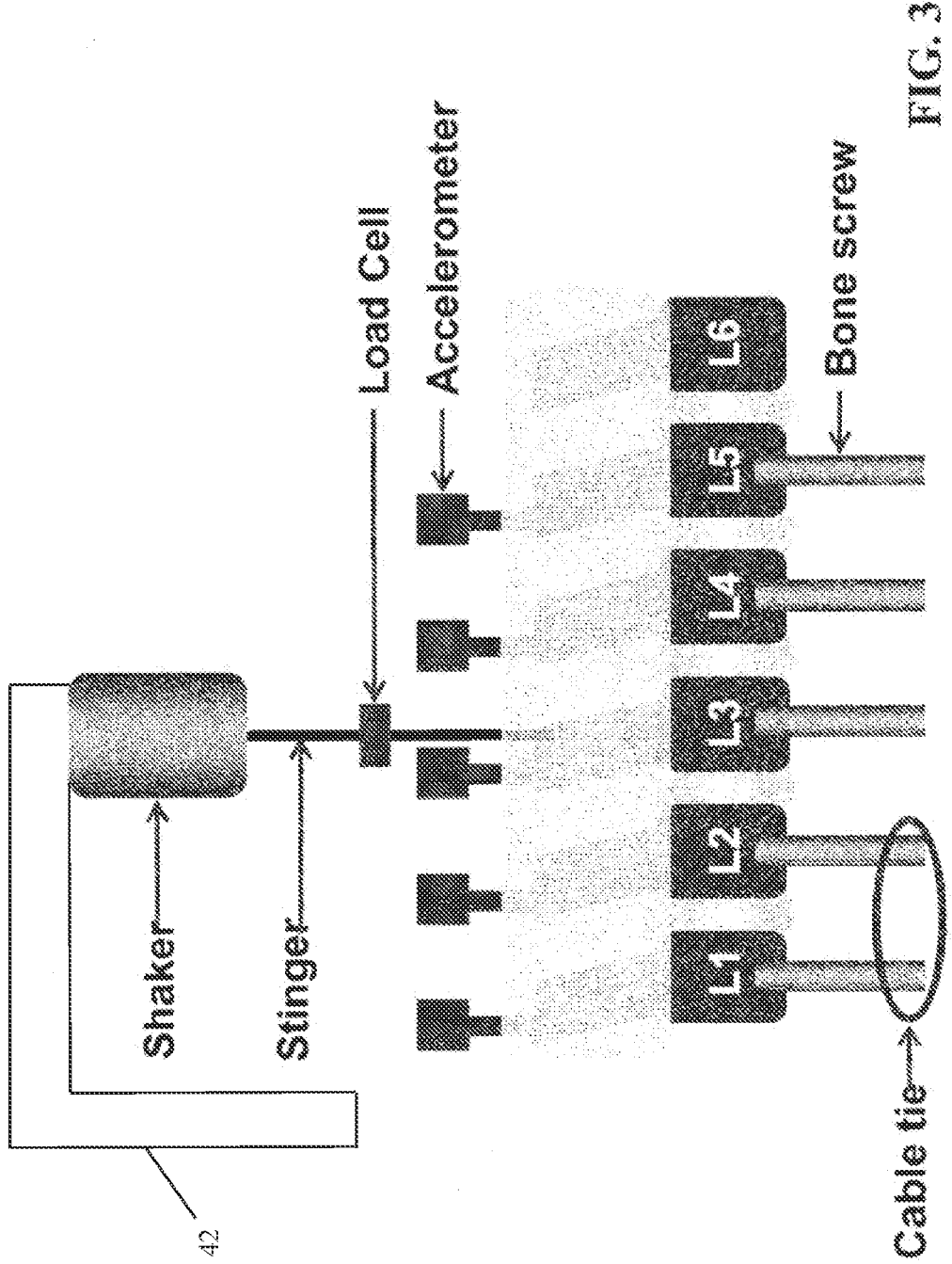
FIG. 3 is a schematic view of an experimental set-up for monitoring the condition of target tissue of a biological skeletal system showing an invasive set up.

The following provides experimental data of animal testing which demonstrates the utility of the method and system. The specific features of the apparatus and method described in the example are not intended to limit the generality of the broadest claim. Six landrace pigs of approximately 70 kg each were sacrificed. Each animal was eviscerated and the anterior soft tissues of the spine removed. A schematic of the following setup is shown in FIG. 3. Pedicle screws (CD Horizon M8 screws, Medtronic, Minneapolis, Minn.) were drilled into the midline of L1-5 inclusive, their caps installed and their saddles aligned to the midline. The soft tissues immediately posterior to the spinous processes were then removed and screws drilled into the midline of each process. To these screws, triaxial accelerometers (356A35, PCB Piezoelectronics Inc., Depew, N.Y.) were mounted so that the following orientations were shared: dorsoventral axes (x), mediolateral axis (y), cephalocaudal axis (z). Each pig was then placed in a sternal position on a rigid table and their hind quarters supported by a sling.

Vibration Application

Figure 4:
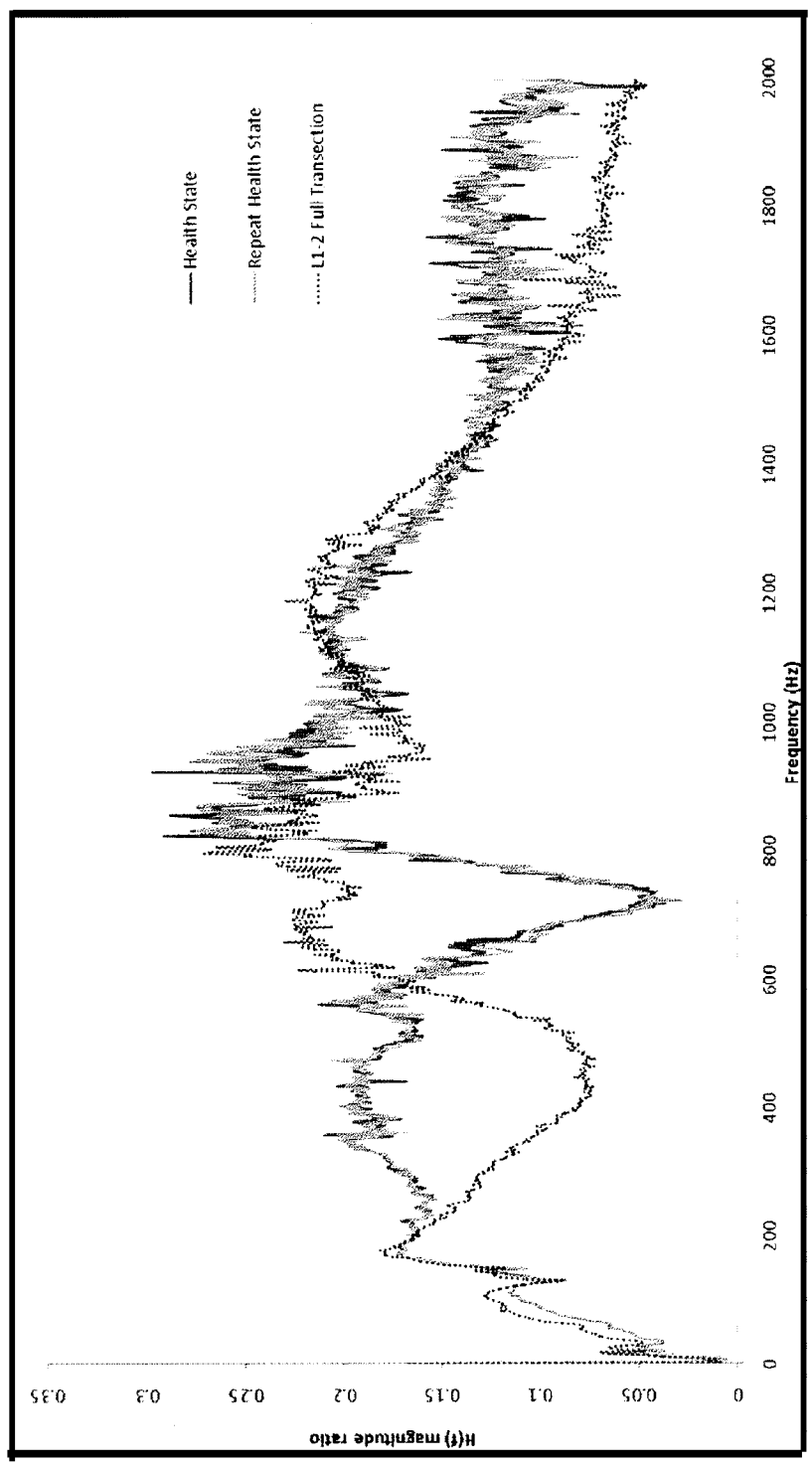
FIG. 4 is a plot of the frequency response function of a structure under test in different structural/functional states.

Vibration was provided by an electromechanical shaker (LW-126-13, Labworks, Costa Mesa, Calif.) which was inverted and suspended above the animal by a rigid cross beam 42 (FIG. 3). A threaded stainless steel rod (i.e. stinger) was used to connect the shaker to the L3 vertebrae by a pincer clamp. The force of the applied vibrations was quantified by a piezoelectrical load cell (208C02, PCB Piezoelectronics Inc., Depew, N.Y.) placed in series with the stinger. A commercial vibration system (Spectral Dynamics, San Jose, Calif.) was used to control shaker output which consisted of bursts of excitation of random frequencies spanning 0-2000. For a single trial, ten bursts were provided with a 1.00 second gap and the resulting signals averaged (total time per trial <60 seconds). Signals from each accelerometer axis and the load cell were obtained at 5120 Hz/channel. For each of the resulting 15 accelerometer sensor axes, the frequency response function (magnitude and phase) was obtained by known calculations. For each single trial, 30 signals were obtained (15 accelerometers×3 axes). Examples of collected FRF data can be seen in FIG. 4.

Health and Damage States

Prepared in the above manner, the spine of each animal was considered to be "healthy". From this state, 7 damage states were created (FIG. 5). Specifically, four reversible damage states were created by linking of two adjacent vertebrae (L1-2 or L2-3 or L3-4 or L4-5). Linkage was achieved by threading a plastic cable tie through the eyelets of the anterior pedicle screws then tightening the tie to a standardized length (FIG. 3). Any alteration in the spine's structure caused by these linkages was presumed to be reversible in that the cable tie could be cut off and the vertebrae able to return to their pre-linkage state (i.e. healthy). Three non-reversible damage states were also created in each disc by inserting a #12 scalpel into the anterior midline (disc stab), extending the stab to transect the left lateral half of the disc (½ transection) then extending that to a full disc transaction (full transaction).

Experimental Protocol

For each animal, 20 structural states were created (FIG. 5) and FRF data collected in each state using three different vibration intensities. The order in which these different structural states were created in each animal is shown in FIG. 5. In brief, testing occurred as follows: creation of single-pair reversible lesions interposed by healthy states, creation of dual pair reversible lesions interposed by healthy states and creation of irreversible lesions. For healthy states, 10 sets of FRF data were collected at three different vibration intensities while for damage states, 5 sets of FRF data were collected for each intensity. In total, 525 sets of FRF data were collected for each animal.

Data Analysis

Using an approach described by Zang et al. (Zang, C., Friswell, M. I. Imregun, M., 2007. Structural Health Monitoring and Damage Assessment Using Frequency Response Correlation Criteria. Journal of Engineering Mechanics 133 (9), 981), the Global Shape Criterion and the Global Amplitude Criterion were calculated between FRF data from each damage state and the prior healthy state. Because the resulting calculation provides a correlation coefficient for shape and amplitude for each frequency under consideration, window-average integration was used to create representative correlations for each of 10 equally divided regions of the frequency range. These regional correlation values, described by Zang et al. as damage indicators, were then used as input to a radial-basis function neural network. This type of network consists of input, hidden and output nodes. In this project, the radial-basis network utilized 20 input nodes (two damage indictors for 10 analysis windows), 200 hidden nodes (arbitrary), and 8 output nodes (a.k.a diagnostic nodes) representing structural health (1), damage location (2-5) and damage magnitude (6-8) (FIG. 5).

The validity of the above procedures to generate damage indicators and then make diagnostic decisions via a neural network was assessed by applying these methods to the same data set employed by Zang et al. 100% agreement was achieved.

To train the neural network in this project, damage indicators were generated for 80% of trials obtained from each structural state (FIG. 5). To test the neural network's ability to assign FRF data to the appropriate diagnostic node(s), damage indicators were then generated for the remaining 20% of trials and used as input into the neural network (FIG. 5). For each group of trials used to train, then test, the network, an equal number of trials from each of three different vibration intensities were included. For each test trial evaluated by the neural network, a numeric value was assigned to each of the 8 output nodes. Node values of greater than 0.49 were considered to be a positive assignment of the FRF data to that diagnostic node. In this way, the output from the network resulted in a binary assignment (0,1) for each diagnostic node. No limitations were placed on binary value assignments by the network—a value of "1" could be provided for a single diagnostic node, multiple nodes, all 8 nodes, or no nodes at all ("0" value assigned to all nodes).

The total number of expected assignments to each diagnostic node were then determined (FIG. 5) as were the number of actual assignments made by the network to those nodes. The actual node assignments were then categorized into true positives (damage present, damage diagnosed), false positives (damage absent, damage diagnosed), true negatives (damage absent, damage undiagnosed), and false negatives (damage present, damage undiagnosed) then expressed over a denominator of the total possible assignments for each of these four categories (Table 6). The sensitivity and specificity of the neural network were then calculated (sensitivity=true positives/(true positives+false negatives; specificity true=negatives/(false positives+true negatives).

Results

Figure 7:
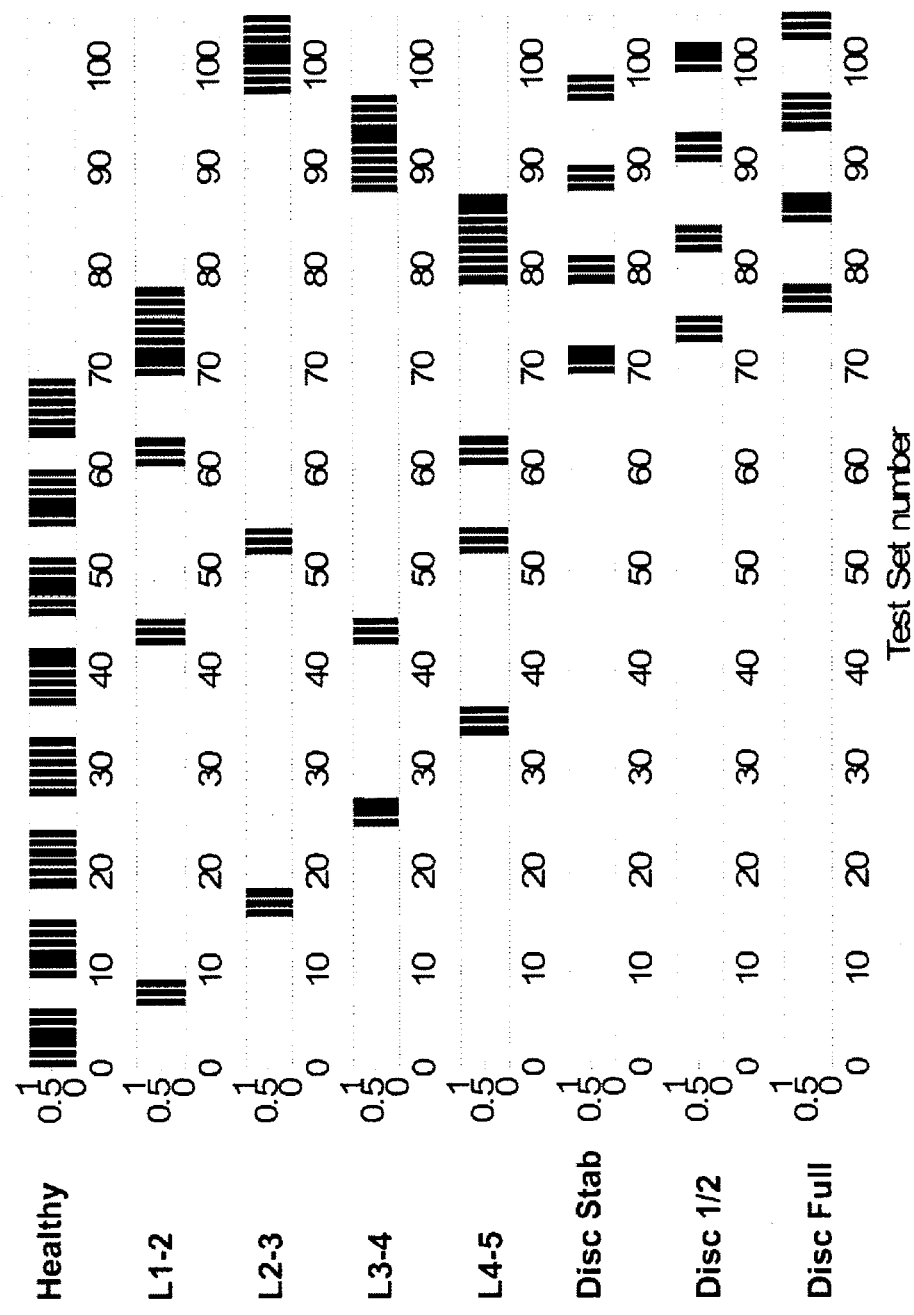
FIG. 7 is a plot of test results.

Each test trial processed by the neural network resulted in an assignment of a binary value to any, or none, of 8 diagnostic nodes. Using data from all three accelerometer axes, an example showing the expected and actual node assignments for pig number 1 is plotted in FIG. 7. In FIG. 7, the 8 possible diagnostic nodes are visualized as separate rows running from left to right with each test trial represented on the x-axis. For any given test trial, the diagnostic node(s) assigned to that trial appear as a vertical bar(s) with a value of "1".

Health States

As can be seen in FIG. 7 and FIG. 5, when a healthy state was expected, (e.g. trial numbers 1-6), the neural network assigned each trial correctly to node 1 (healthy) without concurrent assignment to any other node (damaged). In this example, the neural network performed equally well for all other trials where a healthy state was expected (trial numbers 1-6, 10-15, 19-24, 28-33, 37-42, 46-51, 55-60, 64-69).

Reversible Lesions States

When a single pair of vertebrae was linked together, the neural network correctly assigned FRF data to the diagnostic node corresponding to the location of the lesion without additional assignment to any other node. For example, when L1-L2 were linked together, the neural network correctly assigned trials 1-6 to the diagnostic node indicating the presence of damage at L1-L2 (node 2). When the links were removed, the neural network correctly assigned the FRF data exclusively to the diagnostic node corresponding to the healthy state (node 1). In this example (FIG. 3), the neural network performed equally well for all situations when a single pair of vertebrae were linked together then subsequently released (FIG. 3, trial numbers 1-6, 10-15, 19-24, 28-33, 37-42).

Multiple Reversible Lesions

When two discrete pairs of vertebrae were linked simultaneously, the neural network recognized the presence of two distinct, but simultaneous damage states. For example, when concurrent linkages were created between L1-L2 and L3-L4, the neural network correctly assigned FRF data from trials 43-45 to diagnostic nodes 2 and 4. When these linkages were removed, the FRF data were assigned correctly to diagnostic node 1 (healthy). As can be seen in FIG. 3, correct classification was achieved for all tests where dual damage sites were present.

Non-Reversible Lesions

Trials 70-105 represent FRF data from increasing magnitudes of disc injury caused by progressively larger scalpel insertions into four different lumbar discs. Due to the irreversible nature of these injuries, the neural network was not expected to assign any FRF data to the healthy state (node 1). Instead, the neural network assigned multiple nodes representing lesion magnitude and lesion location. For example, in FIG. 3, it can be seen that when a stab injury is provided to L1-2, FRF data from trials 70-72 are assigned correctly and concurrently to diagnostic nodes representing L1-2 damage (node 2) as well as stab injury (node 6). When half transaction and full transaction were created in the same disc, the network assigned FRF data correctly to nodes representing increasing injury magnitude (nodes 7 then 8) while assigning a node concurrently in recognition that all these three damage magnitudes occurred at L1-L2. FIG. 7 also demonstrates the same pattern of simultaneous recognition of injury location and magnitude for injuries created in each of the three remaining discs.

Diagnostic Results for all Animals

To more easily represent the information visualized in FIG. 3 for all 6 animals, the diagnostic node assignments for each animal were categorized as true positive, true negative, false positive and false negative (FIG. 8). Recall that the neural network is not limited to assigning FRF data in any way—singular, multiple or null node assignments are possible.

As can be seen in FIG. 8, the neural network performed perfectly for 2 of 6 animals when data from all three accelerometer axes were considered. This represents zero error in 1680 node decisions. When each axis was considered separately, the neural network was perfect for 3 of 18 data sets.

When the neural network did not perform perfectly, very few errors were made. When all axes were considered simultaneously, only 10 errors were made in all animals out of 5040 potential node assignments (FIG. 8). When each axis was considered individually, the axis parallel to the principle axis of shaker excitation (x-axis) had the fewest errors (11/5040). These categorical data were then expressed as sensitivity and specificity which each ranged from 0.994-1.00 (FIG. 9).

Discussion

The results of this investigation show that vibration applied at a single point in the spine, then recorded simultaneously at multiple spinal locations, generates FRF data containing sufficient information to identify the presence, location and magnitude of structural damage within the spine.

As the structural health monitoring system employed in this study was able to differentiate between 20 unique structural states, it would be unlikely that this outcome was the result of a continuous change in a single FRF characteristic (e.g. changing amplitude at a given frequency). While specific FRF characteristics may respond directly to damage magnitude, visual inspection of FRF data sets (FIG. 4) and our results suggest that the responsiveness of FRF data is multi-factorial and may include complex responses in amplitude and shape that occur at multiple frequencies. Indeed, the ability of the system to differentiate between multiple damage states at multiple geographic locations suggests the presence of unique frequency responses for individual spinal segments. It should also be emphasized that the system's ability to detect the presence and location of two vertebrae linked together, and then identify a return to normal when the linkage was released, suggests that structural health monitoring has the potential to assess dynamic and/or temporary alterations in spinal function such as those caused by muscle contraction. Although FRF data appears to be a robust and sensitive indicator of the presence, location and magnitude of structure change in the spine, the neural network used to process FRF does not identify the particular characteristics within FRF response that are specific to a given structural alteration.

We use on average 10 N throughout the frequency system. Applied forces of this magnitude, combined with the need to apply these forces in multiple locations if regional mapping is performed, may cause viscoelastic responses and subsequent observer-effects. In comparison, the forces and total testing times associated with the SIMO technique described here appear to have little viscoelastic impact; FRF data are highly reproducible even in the presence of structural damage where it could imagined that applied vibrations may exacerbate existing damage state. It should be noted that exposure to vibration in the SIMO technique described here is significantly less than that associated with vibration-induced injury.

Although there may be circumstances where a mounting scheme directly to the spine could be used in humans, its application in large populations would require non-invasive fastening techniques with consideration given to potential artifacts and/or decreased response created by the separation of the sensor and underlying bone via the skin. In addition, use of larger, triaxial accelerometers with a non-rigid attachment can make sensor alignment problematic. Given that our results indicate FRF data from the x-axis alone performs similarly compared to FRF data from all three axes combined, uniaxial sensors may be advantageous.

Finally, structural health monitoring, like many other diagnostic procedures, requires knowledge of the baseline condition to detect change within the system. Unique FRF signatures for specific structural damage or pathology determined by routine investigations, baseline data from normal populations, or predictions of normal responses from mathematical models, may be used as baseline data for diagnosis of an altered structural state.

Example 2

The system and method were tested on 4 human cadaver subjects. The results are in agreement with those obtained from the studies in pigs. In summary, the signals are extremely reliable as they remain stable in multiple trials for the same condition. When the condition changes (e.g. voluntary muscle contraction), the changes in the signal are easily detected.

Figure 10:
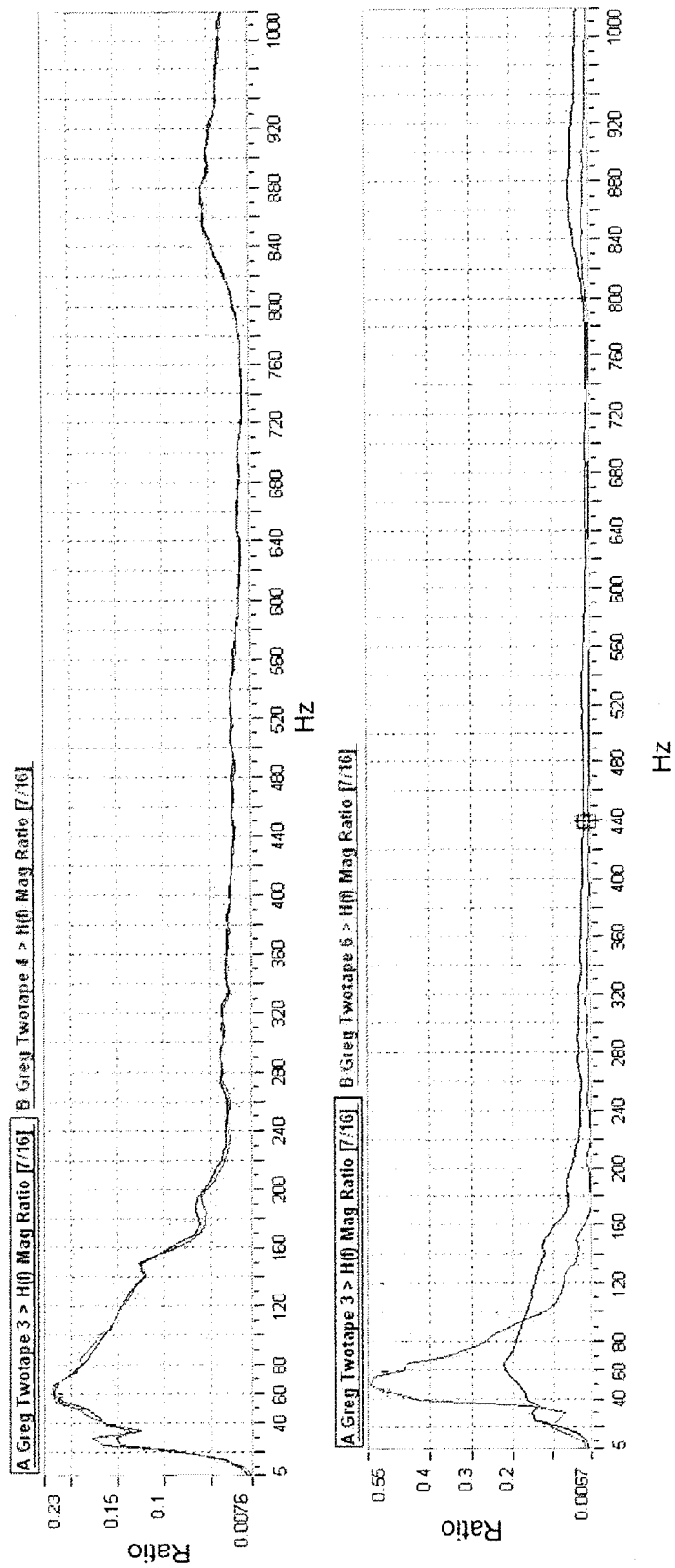
FIGS. 10-12 illustrate test results in human cadavers.
Figure 11:
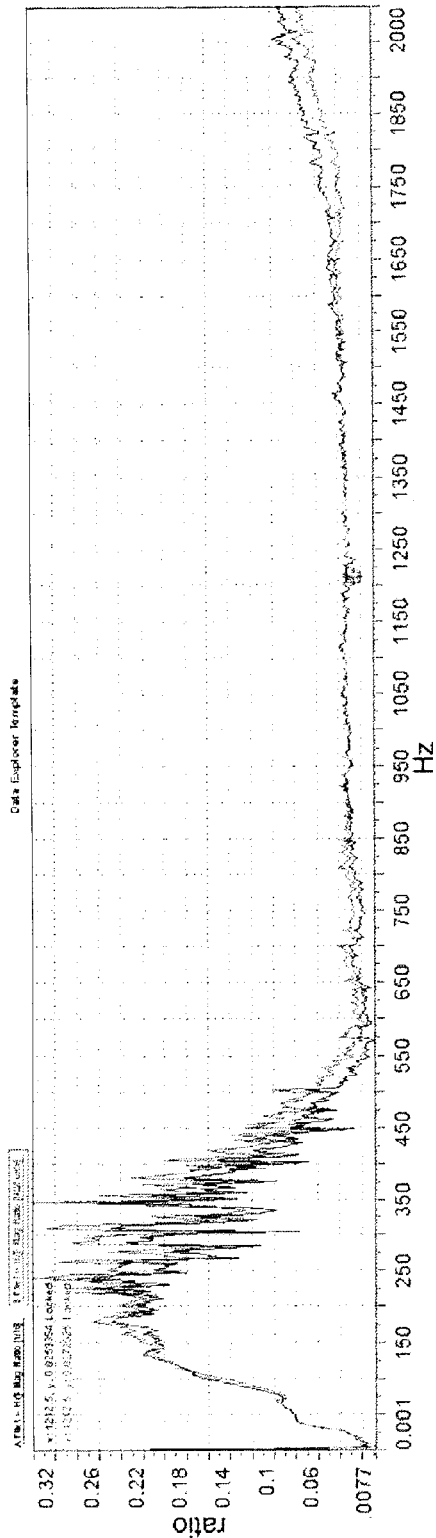
Figure 12:
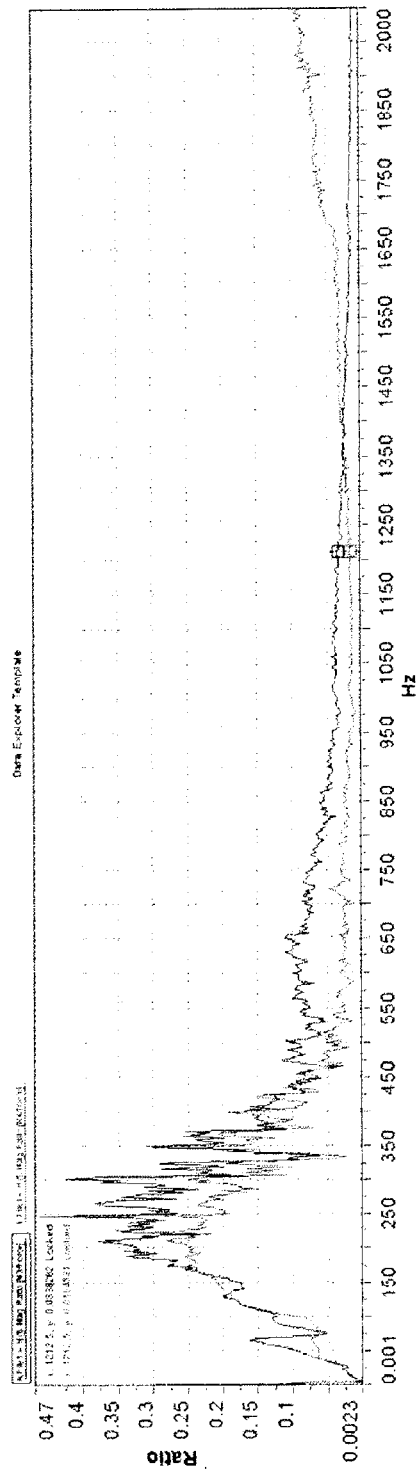

FIGS. 10-12 illustrate results from human testing. All equipment that was used with the pig testing was the same for human cadaver testing. Similarly, all settings to perform the testing, collect data and analyze data were equal between pig cadavers and human cadavers such as vibration input, data recording, data processing. Data has been collected on 4 human cadavers. The only difference is that in the human cadaver, vibration was provided from 0 to 1000 Hz.

In FIG. 10, top chart, the curves show the frequency response of a human vertebra. The two curves were taken at different times but under the same experimental conditions, indicating the consistency of the response. In the lower chart, the curves indicate the frequency response of a human vertebra with and without voluntary contraction of the gluteal muscle. The curves show that different states of the human vertebra, or structures which connect to the vertebrae, yield different response curves.

Through palpation, the spinous processes of L1-5 in the human cadavers were identified and vibration applied in the typical fashion by placing the stinger of the shaker on the L1 spinous process. Two small gauge needles were placed through the skin and into each of spinous processes L2-5. After collecting and processing data (FIG. 11), one needle from each spinous was removed and then replaced with a sensor adhered to the skin surface overtop of the spinous in question. Data was then recorded as described previously (FIG. 12). FIG. 11 shows that placing two needles in the spinous process of a human cadaver causes the needles to vibrate equally. That is, if two needles are in a rigid body, they vibrate equally. FIG. 12 shows a trace from a needle in the vertebrae (as above) but then also from another sensor mounted on the skin. The two appear similar thereby suggesting that the vibration signals obtained from the skin are very much like the signals obtained from the bone directly with the needle.

The disclosed results show that the disclosed process and apparatus may identify structural or functional status of the skeleton of a human being. Pig results are relevant because the spinal anatomy of pigs and humans is very similar. Further, human testing thus far shows that vibration input into humans yields the same types of responses to that vibration as are seen in the pig. Results on the spine may be extrapolated to other skeletal components since rigid skeleton components are expected to respond alike to similar inputs and with similar conditions. The shape of the bone (vertebrae, femur) is irrelevant to the process. Results show that disruption of ligaments and discs as well as changing the stiffness of the structures under test may be identified. Theoretically, any change to the system (connectors gained/lost, mass, disruption of the solid body, changes in stiffness etc.) will all have an effect on how the solid body responds to vibration.

The method and system may also be applied to detect injury processes or pathologies that are not currently known and that affect the system's response to vibration. In this case, modeling of vibration traces may predict what parameters would need to change to provide a specific response. In that way, new diagnoses may be established. Hence, the output of the measurement has utility in itself.

Immaterial modifications may be made to the embodiments described here without departing from what is covered by the claims. In the claims, the word "comprising" is used in its inclusive sense and does not exclude other elements being present. The indefinite article "a" before a claim feature does not exclude more than one of the feature being present. Each one of the individual features described here may be used in one or more embodiments and is not, by virtue only of being described here, to be construed as essential to all embodiments as defined by the claims.

What is claimed is:

1. A method of monitoring target tissue of a biological skeletal system including surrounding tissues and skin, the method comprising:

applying a mechanical excitation to a portion of the biological skeletal system using a frequency controlled electromechanical shaker placed in contact with the portion of the biological skeletal system to generate a mechanical wave that passes through the target tissue, the target tissue modulating the mechanical wave to produce a response of the target tissue to the mechanical wave, the response comprising a movement of bone within the target tissue as a solid body;

measuring the response of the target tissue to the mechanical excitation using sensors that are sampled at a plurality of locations distributed across the biological skeletal system, the measuring comprising measuring one or more of acceleration, displacement and velocity of the movement of the bone; and determining structural or functional status of the target tissue from the measured response by comparing the measured response with a standard indicative of the structural or functional status of the target tissue.

2. The method of claim 1 in which the target tissue is a vertebral column.

3. The method of claim 1 in which the measured response is measured with one or more sensors through skin overlying the target tissue.

4. The method of claim 1 in which the mechanical excitation includes frequencies in the range from 0 to 2000 Hz.

5. The method of claim 1 further comprising measuring the mechanical excitation applied to the portion of the biological excitation system to generate an input signal measurement, processing the measured response of the target tissue by comparing the measured response to the input signal measurement and determining structural or functional status of the target tissue from the measured response after comparison with the input signal measurement.

6. The method of claim 1 in which determining a property of the target tissue from the measurement comprises comparing the measurement to a previously measured response to identify structural and/or functional changes in the skeletal system.

7. The method of claim 1 in which the target tissue comprises one or more vertebra.

8. A system for monitoring the condition of target tissue of a biological skeletal system, the target tissue comprising vertebra and surrounding tissue, the system comprising:

a frequency controlled electromechanical shaker having a movement inducing output for applying a mechanical excitation to a portion of the biological skeletal system to generate a mechanical wave that is capable of passing through the target tissue and being modulated by the target tissue to produce a response of the target tissue to the mechanical wave, the response comprising a movement of bone within the tar et tissue as a solid body;

plural sensors adapted to be distributed at a plurality of locations on the biological skeletal system including the surrounding tissues and skin for sensing the response by measuring one or more of acceleration, displacement and velocity of the movement of the bone; and a processing system connected to receive output of the one or more sensors and produce a representation of the response.

9. The system of claim 8 in which the processing system is adapted to sample the sensors simultaneously.

10. The system of claim 8 in which the plural sensors are adapted to be located on, or affixed to, a vertebral column.

11. The system of claim 8 in which the plural sensors are adapted to sense the response through skin overlying the target tissue.

12. The system of claim 8 in which the mechanical excitation includes frequencies in the range from 0 to 2000 Hz.

13. The system of claim 8 further comprising a sensor of the mechanical excitation prior to the modulation of the mechanical wave by the portion of the biological skeletal system, surrounding tissues and skin, the processing system being responsive to signals from the sensor and to determine a property of the target tissue from the response after processing of the response by comparing the response to the signals from the sensor.

14. The system of claim 8 in which the processing system is configured to determine a property of the target tissue from the response.

15. The system of claim 14 in which the processing system is configured to determine the property of the target tissue from the response by comparing the response to a previously measured response to identify structural changes in the skeletal system.

16. The system of claim 8 in which the one or more sensors comprise an ultrasound sensor.

17. The method of claim 1 in which the anchored frequency controlled electromechanical shaker applies a mechanical excitation in user defined bursts of excitation having a controlled length, frequency content and repetition.

18. The method of claim 17 in which the bursts of excitation each last at least one second.

19. The method of claim 18 in which the bursts of excitation each last at least 10 seconds.

20. The method of claim 1 in which the sensors comprise an ultrasound sensor.

21. The method of claim 20 further comprising measuring displacement of the target tissue using the ultrasound sensor.

22. The method of claim 21 in which the biological skeletal system comprises one or more vertebra.

23. The method of claim 1 in which the frequency controlled electromechanical shaker is anchored to a rigid body.

24. The method of claim 1 in which the sensors are sampled at a plurality of locations distributed across respective bones jointed by joints of the biological skeletal system.

25. The system of claim 8 in which the frequency controlled electromechanical shaker is anchored to a rigid body.

26. The system of claim 8 in which the sensors are sampled at a plurality of locations distributed across respective bones jointed by joints of the biological skeletal system.

* * * * *